United States Patent [19]

Srapeniants et al.

[11] 4,268,754
[45] May 19, 1981

[54] RADIOACTIVATION METHOD FOR SIMULTANEOUS DETERMINATION OF NITROGEN, PHOSPHORUS AND POTASSIUM CONTENT IN PLANTS AND FERTILIZERS

[76] Inventors: Rigo A. Srapeniants, B. Pereyaslavskaya ulitsa, 15, kv. 140; Igor B. Saveliev, Preobrazhensky val, 24, kv. 76; Jury L. Kovtun, Preobrazhensky val, 24, kv. 70; Alexandr V. Sidorov, Velozavodskaya ulitsa, 2, korpus 4, kv. 26; Kim S. Tsagolov, ulitsa Gostinichnava, 9v, kv. 13; Nadezhda N. Miroshnikova, Altufievskoe shosse, 95b, kv. 164, all of Moscow, U.S.S.R.

[21] Appl. No.: 28,397

[22] Filed: Apr. 9, 1979

[51] Int. Cl.³ ............................................. G01T 3/00
[52] U.S. Cl. ................................................. 250/391
[58] Field of Search ............... 250/253, 390, 391, 392; 176/19 R

[56] References Cited

U.S. PATENT DOCUMENTS 3,124,679  3/1964  Tittman et al. ..................... 250/390
4,053,771  10/1977  Aude et al. ......................... 250/391

OTHER PUBLICATIONS

Nadkarni, R. A. and Morrison, G. H., "Multielement Instrumental Neutron Activation Analysis of Biological Materials", *Analytical Chemistry*, vol. 45, No. 11, (Sep. 1973), pp. 1957-1960.

*Primary Examiner*—Alfred E. Smith
*Assistant Examiner*—Janice A. Howell
*Attorney, Agent, or Firm*—Steinberg & Raskin

[57] ABSTRACT

According to the invention, the radioactivation method for simultaneous determination of the nitrogen, phosphorus and potassium content in plants and fertilizers consists in exposing samples to be analyzed and standard samples to neutron irradiation and recording the spectra of the gamma radiation induced in said samples, whereupon the samples are laid aside for a period of time determined by the half-life of the interfering isotope. This is followed by again recording the spectra of the samples being analyzed and of the standard samples and superposing the first and second spectra of the samples being analyzed and of the standard samples. These spectra are then shifted relative to each other along the energy axis, and the contents of the elements being analyzed are determined by thus comparing the spectra of the samples being analyzed and of the standard samples.

1 Claim, 15 Drawing Figures

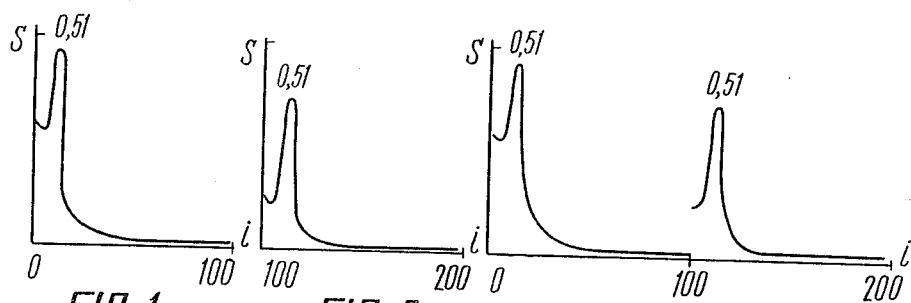
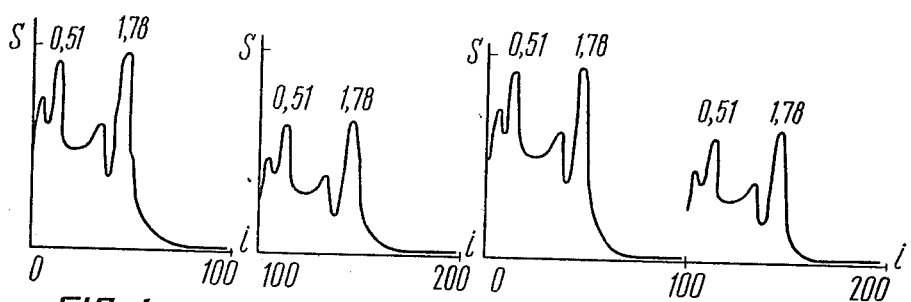
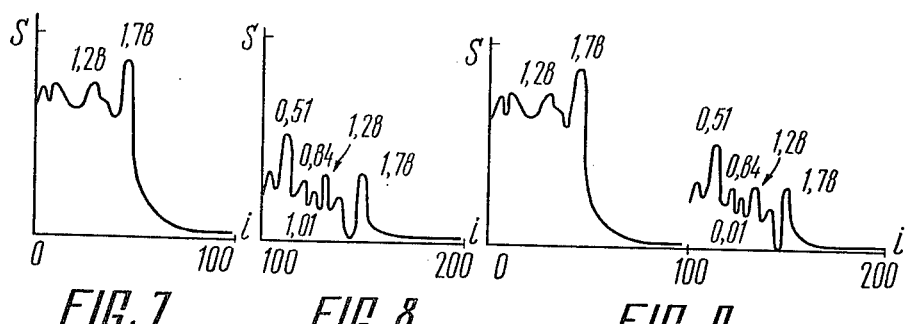

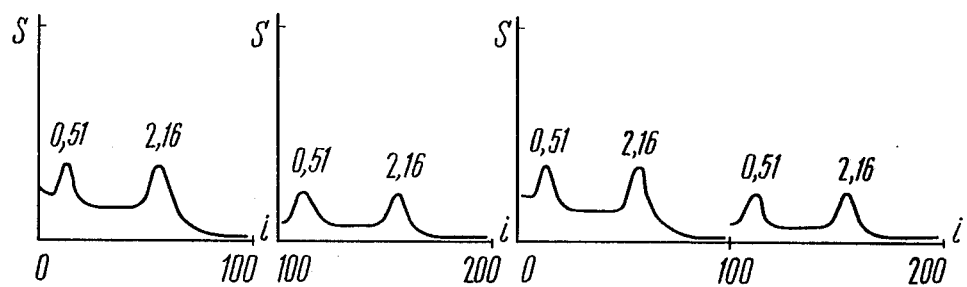
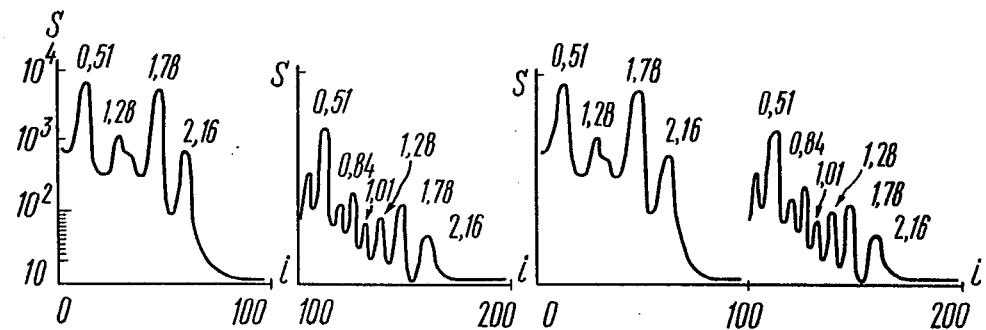

RADIOACTIVATION METHOD FOR SIMULTANEOUS DETERMINATION OF NITROGEN, PHOSPHORUS AND POTASSIUM CONTENT IN PLANTS AND FERTILIZERS

FIELD OF THE INVENTION

The present invention relates to the determination of the content of chemical elements in plants and fertilizers and, more particularly, to radioactivation methods for simultaneous determination of the nitrogen, potassium and phosphorus content in plants and fertilizers. The invention can be used in agriculture and forestry.

BACKGROUND OF THE INVENTION

There is known a method for simultaneous determination of the content of several chemical elements, such as nitrogen, phosphorus and potassium, in plant samples. According to this method, samples to be analyzed and standard samples are exposed to a fast neutron flux. After a certain period of time, the spectrum of the gamma radiation induced in the samples is recorded and analyzed with reference to the spectra of the standard samples by using the least squares method (cf. R. A. Srapenyants, J. L. Kovtoun, E. Vernin, G. Aude, C. Axelrod, "Méthode et installation de dosage automatique par activation neutronique de N, P, K, Ca dans les végétaux", Proceedings of the Symposium on Nuclear Activation Techniques in the Life Sciences, Apr. 10–14, 1972, Bled, Jugoslavia, International Atomic Energy Agency, Vienna, 1972).

The method under review is disadvantageous because of its low accuracy, especially when analyzing plant samples with a silicon content of more than 0.05 percent by weight. This is due to the fact that the phosphorus content is determined from the radioactive isotope $Al^{28}$ which is also produced from silicon as a result of a competitive nuclear reaction. In the case of phosphorus determination, the time between the end of irradiation and the moment the spectrum is taken is such that the contributions of phosphorus and silicon to the spectrum of the irradiated plant sample practically cannot be differentiated.

SUMMARY OF THE INVENTION

It is an object of the present invention to provide a method for simultaneous determination of the nitrogen, phosphorus and potassium content in plants and fertilizers, which would ensure a higher accuracy of the analysis by resorting to repeated recording of the spectra of samples being analyzed and standard samples.

The foregoing object is attained by providing a radioactivation method for simultaneous determination of the nitrogen, phosphorus and potassium content in plants and fertilizers, whereby samples to be analyzed and standard samples are exposed to neutron irradiation, the spectra of gamma radiation induced in said samples are recorded, and the nitrogen, phosphorus and potassium content is determined from said spectra, which method is characterized, according to the invention, in that after recording the spectra, the samples being analyzed and standard samples are laid aside for a period of time determined by the half-life of the interfering isotope, whereupon the spectra of the samples being analyzed and of the standard samples are recorded again, the first and second spectra of the samples being analyzed and of the standard samples are superposed and shifted relative to each other along the energy axis, and the content of the elements being analyzed is determined by comparing the spectra of the samples being analyzed and of the standard samples.

DETAILED DESCRIPTION OF THE INVENTION

The radioactivation method according to the invention is carried out as follows.

Standard samples of nitrogen, phosphorus, potassium and silicon and samples to be analyzed are exposed to a neutron flux emitted by a neutron generator. After a period of time of 1 to 5 minutes, i.e. after a period of time sufficiently long for the decay to take place, the gamma radiation spectrum of the irradiated samples is recorded with the use of spectrometric equipment.

The standard samples and those being analyzed are then laid aside for a second period of time of 5 to 25 minutes, whereafter their spectra are recorded again. The first and second spectra are superposed; the discontinuities of the first spectra are filled with portions of the second spectra of the respective samples, and the first and second spectra are shifted relative to each other along the energy axis. The information thus received is illustrated by the attached plots where i is the channel number proportional to the energy of gamma radiation, and S is the number of pulses recorded in a given channel.

The nitrogen, phosphorus and potassium content is determined by comparing the spectra of the standard samples with those of the samples being analyzed, which is done by using the conventional mathematical methods, such as the least squares method.

The method according to the invention is fundamentally different from conventional methods serving the same purpose in that instead of measuring the actual gamma radiation spectrum, the object of measurements is a composite spectrum produced by superposing two spectra taken after different periods of time. Apart from the information on the gamma radiation energy distribution, the spectra thus superposed also carry information on the change of this distribution with time, which accounts for a higher accuracy of the analysis.

The following table compares the results of analyzing plant samples with the use of the conventional method and the one according to the invention. The analysis covered 4 types of control plant samples, namely, oat, barley, maize and grass mixture. The content of N, P and K in the samples was determined by chemical analysis.

TABLE

| Type of Sample | Chemical Element | Result of Chemical Analysis wt. % | Average Value, wt. % | | Variation Coefficient of Single Measurement, % Relat. | | Absolute Difference from Results of Chemical Analysis % | |
|---|---|---|---|---|---|---|---|---|
| | | | Method According to Invention | Prior Art Method | Method According to Invention | Prior Art Method | Method According to Invention | Prior Art Method |
| 1 | 2 | 3 | 4 | 5 | 6 | 7 | 8 | 9 |
| Oat | N | 2.02 | 2.02 | 2.18 | 1.5 | 3.0 | 0.0 | +8.0 |
| | P | 0.43 | 0.46 | 0.30 | 8.1 | 13.0 | +7.0 | −3.02 |
| | K | 0.51 | 0.56 | 0.57 | 8.8 | 15.1 | +9.8 | +11.8 |
| Grass | N | 3.35–3.41 | 3.50 | 3.39 | 0.9 | 2.8 | +2.6 | 0.0 |
| Mixture | P | 0.30–0.34 | 0.35 | 0.38 | 6.5 | 9.6 | +2.9 | +11.8 |
| | K | 2.10–2.30 | 2.26 | 2.60 | 4.3 | 6.9 | 0.0 | +13.0 |
| Barley | N | 1.94 | 1.95 | 1.94 | 3.0 | 2.7 | +0.5 | 0.0 |
| | P | 0.39 | 0.40 | 0.41 | 7.2 | 16.6 | +2.5 | +5.1 |
| | K | 0.43 | 0.45 | 0.48 | 6.0 | 12.6 | +4.6 | +11.6 |
| Maize | N | 1.62 | 1.64 | 1.64 | 3.2 | 2.7 | +1.2 | +1.2 |
| | P | 0.37 | 0.38 | 0.39 | 7.8 | 10.7 | +2.7 | +5.4 |
| | K | 0.38 | 0.35 | 0.24 | 6.9 | 11.3 | −10.2 | −36.8 |

The foregoing table makes it clear that the discrepancy between the results of the chemical analysis and those obtained with the use of the method according to the invention is not greater than 10 percent; the average discrepancy is 3 percent for N and 5 to 7 percent for P and K. The convergence of the results is also satisfactory, being 3 percent for K and 6 to 9 percent for P and K. On the contrary, the prior art method shows strong deviations in determining P and K, which in a number of cases are as high as 11 to 30 percent; the variation coefficients are often as high as 10 to 15 percent, which is unacceptable.

A better understanding of the present invention will be had from a consideration of the following examples illustrating preferred embodiments thereof.

EXAMPLE 1

Standard samples of nitrogen, phosphorus, silicon and potassium and samples of oat are put into polyethylene capsules of a constant volume, exposed to a neutron flux of 14.5 Mev and put aside for a period of time of 1 to 2 minutes for the decay to take place. A gamma radiation spectrum is taken with the aid of a scintillation detector and a multi-channel pulse-height analyzer; the spectrum is taken in 100 channels of the analyzer. The standard samples and those being analyzed are then laid aside for a second period of time of 16 minutes, whereupon they are transferred to a second detector.

A scintillation gamma radiation spectrum is again taken in 100 channels of the analyzer and added to the first spectra of the respective standard samples and samples being analyzed as channels 101 through 200.

Plots 1 through 15 represent the information thus obtained.

FIG. 1, where i is the channel number proportional to the gamma radiation energy and S is the number of pulses recorded in the channel, shows the spectrum of a standard sample of nitrogen, recorded 2 minutes after the end of the irradiation.

FIG. 2 is plotted in the same coordinates as FIG. 1 and shows the spectrum of the standard sample of nitrogen, recorded 16 minutes after the end of the irradiation.

FIG. 3 is plotted in the same coordinates as FIG. 1 and shows a composite spectrum of the standard sample of nitrogen, produced by adding the first and second spectra together.

FIGS. 4 through 15 are plotted in the same coordinates as FIG. 1 and show first and second spectra, as well as composite spectra of phosphorus, silicon and potassium, and those of the sample being analyzed, obtained as the spectra of FIGS. 1, 2 and 3.

In order to find the concentrations of nitrogen, phosphorus and potassium, the least squares method is used to divide the composite spectrum of the sample subjected to analysis into those of the standard samples.

The period of time between the end of irradiation and the moment the first spectrum is taken is 2 minutes. This period is sufficiently long for short-lived isotopes to decay (this applied, for example, to $N^{16}$ whereof $T_{\frac{1}{2}} = 7.4$ sec); yet this period is short enough for the activity of $Al^{28}$ produced from phosphorus and silicon to be maintained at a reasonably high level ($T_{\frac{1}{2}}$ of $Al^{28}$ is 2.3 min). The second period of time during which the samples are put aside is 16 minutes and is selected with due regard for the decay of the activity of $Al^{28}$.

20 weighed portions of oat were used in the determination of the nitrogen, phosphorus and potassium content. The percentage by weight concentrations of these elements were as follows: N, 2.02; P, 0.46; K, 0.56.

EXAMPLE 2

The analysis is carried out as in Example 1, but this time the object of the analysis is grass mixture.

The percentage by weight concentrations of the three elements are as follows: N, 3.50; P, 0.35; K, 2.26.

EXAMPLE 3

The analysis is carried out as in Example 1, but the object of the analysis is barley.

The percentage by weight concentrations of the three elements are as follows: N, 1.95; P, 0.40; K, 0.45.

EXAMPLE 4

The analysis is carried out as in Example 1, but the object of the analysis is maize.

The percentage by weight concentrations of the three elements are as follows: N, 1.64; P, 0.38; K, 0.35.

What is claimed is:

1. A radioactivation method for simultaneous determination of the nitrogen, phosphorus and potassium content in plants and fertilizers which also contain isotopes which interfere with gamma radiation analysis, said isotopes having a specific half-life, which comprises exposing samples to be analyzed and standard samples to neutron irradiation to induce gamma radiation which is plotted as a spectrum of gamma radiation energy in proportion to number of pulses of the neutron irradiation, recording the spectra of gamma radiation induced in said samples, setting said samples aside for a period of time corresponding to the half-life of the interfering isotope, again exposing said samples being analyzed and said standard samples to neutron irradiation and recording the resulting spectra of gamma radiation, superposing the first and second spectra of the samples being analyzed and standard samples and shifting the same relative to each other along the energy axis, and comparing the spectra of the samples being analyzed and the standard samples to determine the content of the elements being analyzed.

* * * * *